United States Patent
Assmann et al.

(10) Patent No.: US 8,355,549 B2
(45) Date of Patent: Jan. 15, 2013

(54) METHOD AND MEDICAL DEVICE FOR CONTROLLING DATA ACQUISITION OR DATA PROCESSING THEREIN

(75) Inventors: Stefan Assmann, Erlangen (DE); Annegret Thomas, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 958 days.

(21) Appl. No.: 12/117,354

(22) Filed: May 8, 2008

(65) Prior Publication Data
US 2008/0279432 A1 Nov. 13, 2008

(30) Foreign Application Priority Data
May 11, 2007 (DE) .................. 10 2007 022 087

(51) Int. Cl.
G03B 42/08 (2006.01)
G06K 9/00 (2006.01)
(52) U.S. Cl. ........................................ 382/128
(58) Field of Classification Search .................. 382/128
See application file for complete search history.

(56) References Cited

U.S. PATENT DOCUMENTS

| | | | | |
|---|---|---|---|---|
| 4,509,526 | A * | 4/1985 | Barnes et al. | 600/456 |
| 6,975,897 | B2 * | 12/2005 | Knoplioch et al. | 600/425 |
| 7,421,140 | B2 * | 9/2008 | Rottem | 382/254 |
| 2004/0090451 | A1 * | 5/2004 | Lay et al. | 345/713 |
| 2004/0158205 | A1 * | 8/2004 | Savage | 604/151 |
| 2006/0040245 | A1 * | 2/2006 | Airola et al. | 434/262 |

OTHER PUBLICATIONS

"Einsatzfelder von Workflow—Management im Krankenhaus", Calzo (1998).

* cited by examiner

Primary Examiner — Clayton E LaBalle
Assistant Examiner — Leon W Rhodes, Jr.
(74) Attorney, Agent, or Firm — Schiff Hardin LLP

(57) ABSTRACT

In a method to control the data acquisition and/or the data processing in at least one medical device, in particular to control the image data acquisition and/or the image data processing in a medical image data acquisition device, at least one work step already effected and/or still to be effected by an operator at a computer in the framework of controlling the data acquisition and/or the data processing is determined and/or analyzed by at least one program, and the operator is assisted dependent on the determination and/or analysis result.

14 Claims, 2 Drawing Sheets

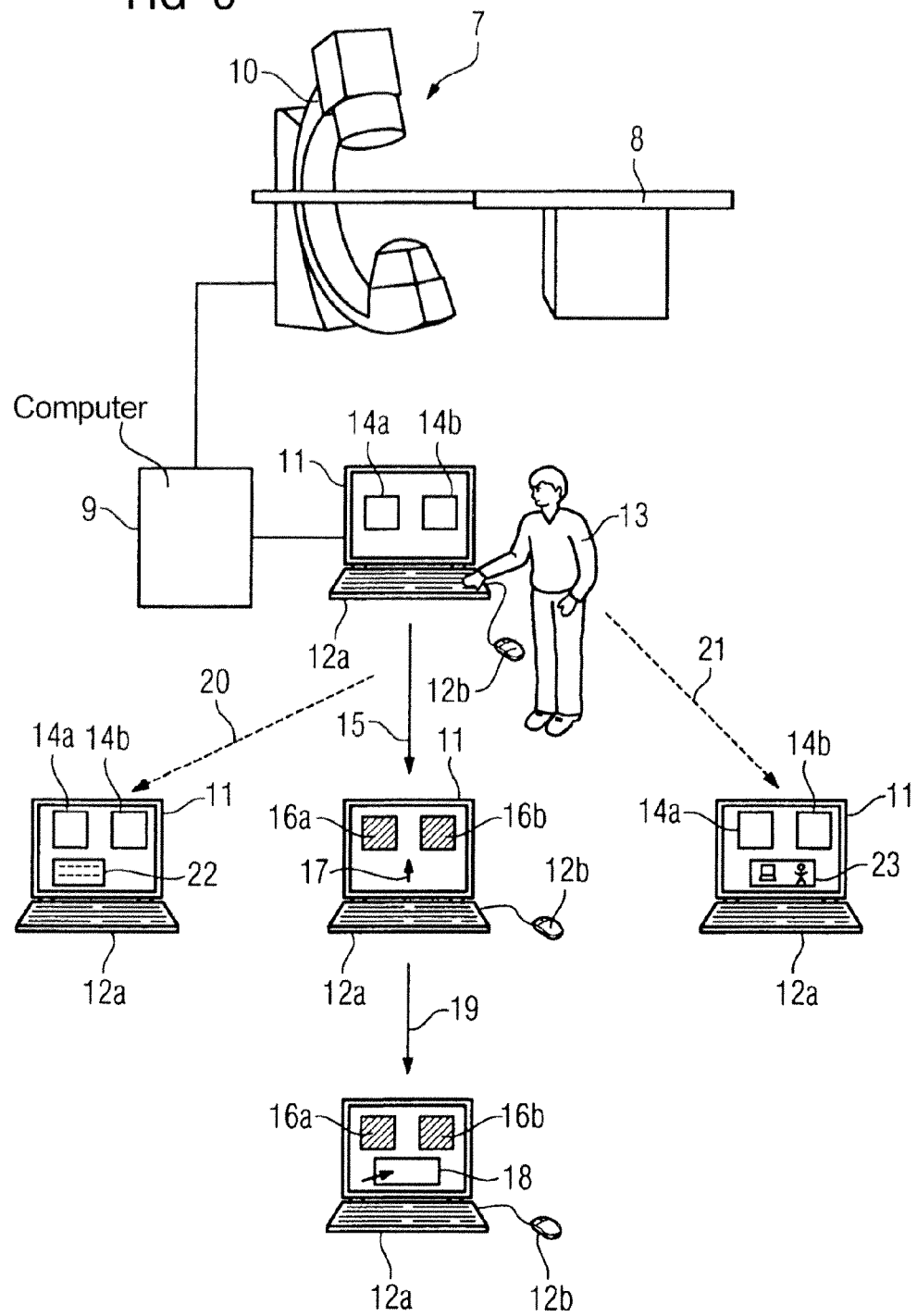

METHOD AND MEDICAL DEVICE FOR CONTROLLING DATA ACQUISITION OR DATA PROCESSING THEREIN

BACKGROUND OF THE INVENTION

1. Field of the Invention

The present invention concerns a method for controlling the data acquisition and/or the data processing in at least one medical device, in particular to control the image data acquisition and/or the image data processing in a medical image data acquisition device, as well as an associated medical device.

2. Description of the Prior Art

Often a number of work steps or very complex workflows must be implemented in the framework of the data acquisition with medical devices, for example data acquisition with magnetic resonance apparatuses or computed tomography apparatuses. This pertains both to data acquisition and to the subsequent processing of the data in order to obtain finished, reconstructed image data or image data that are optimally prepared, for a presentation, for example.

An operator or user who controls the acquisition of the measurement data and/or is entrusted with the preparation must therefore have comprehensive knowledge or look up information in a manual or other text documents in the event that the user requires help. In some cases, online help is also provided from which an overview of the available technical possibilities can be learned. However, this information must be retrieved separately and a search through the help database with keywords is required in order to obtain the actual required information.

Moreover, in medical devices it is mandatory to provide standardized operating instructions at each workspace, thus at every control console or workstation for post-processing of acquired measurement data. These standardized operating instructions (SOPs) are text documents that not intelligible to every operator at first glance and which are difficult to store such that accessibility for all operators exists as well as a constant availability.

SUMMARY OF THE INVENTION

An object of the present invention is to provide a method that is improved with regard to the above considerations as well as an associated medical device.

This object is achieved in accordance with the invention by a method of the aforementioned type wherein at least one work step that is already effected and/or still to be effected by an operator at a computer in the framework of the control of the data acquisition and/or the data processing is determined and/or analyzed by at least one program, and the operator is assisted dependent on the determination and/or analysis result.

The operator (who is located at a computer such as, for example, at a console to control an image data acquisition at a magnetic resonance apparatus or the like) is thus automatically or interactively assisted in his actions by the program.

The program, which is stored on the computer or to which the computer has access, establishes (as an interactive aid) at which point in the workflow the user is situated. The actions of the user are tracked by the program (which can be an extensive program package with multiple routines and can be stored distributed to multiple locations) and, for example, using already-effected work steps or using a protocol selected for a data acquisition it can be established which following work steps are still pending. The program can possibly associate work steps already effected with database data by a comparison, or can identify the work steps that have already effected as a specific work step.

The work steps can be of different types. This term is to be understood in a broad sense. For example, they can be individual steps in the post-processing of image data or steps in the acquisition of image data sequences or the processing of examination protocols.

The program tracks the work steps in the background (in a monitoring mode) or upon request by the operator, determines the work steps, and analyzes them, so that the operator is assisted. The assistance thus depends on which work step was effected or was detected by the program as still to be effected, and/or whether the program, in the framework of the analysis, has detected atypical inputs or errors on the part of the operator in a work step.

Moreover, the operator can inventively be assisted depending on a confirmation of an assistance offered by the program and/or dependent on an assistance request on the part of the operator, in particular by calling a help function offered by the program and/or via inputs in a help function.

The interactive assistance of the operator accordingly ensues, for example, such that the program generates a confirmation request, for example such that the operator is asked whether he or she requires help, which request he or she can confirm by clicking a corresponding field by means of an input tool, for example. Moreover, the operator can actively request assistance. For example, if he is unsure in the image data acquisition or processing the operator can thus request help by starting the program or shifting it into an active state, for example by clicking on an icon or another desktop symbol or by a corresponding selection in a menu bar. The program can track the actions of the user in the background at any time or only after an activation in order to then offer assistance when this is actually desired, as the operator makes this clear via the request.

According to the invention, the operator can be assisted by simulation and/or automatic implementation of at least one subsequent work step by the program. In this case a subsequent workflow step proceeding from the operator's current position in the workflow is thus directly simulated for the user who requires help. For example, if a subsequent step recognized as reasonable by the program is a segmentation step for image data, the system or the computer can take over the mouse or another operating tool and wholly automatically initiate the segmentation in a comprehensible manner. For example, if data acquisition is reasonable, subsequent data acquisition steps (for example a detail acquisition of a body region with distinctive features in the framework of a sequence with image acquisitions) can be implemented automatically or can be simulated in a comprehensible manner for the operator in a similar form.

A subsequent work step can be implemented automatically (possibly after a preceding simulation) dependent on a confirmation and/or an indication of consent by the operator. For example, it is possible that a segmentation of image data is simulated to an operator on the monitor, whereupon the operator is asked by the program whether this segmentation should actually take place. The operator can confirm this by clicking or by a speech input or the like. An OK button or the like can also directly appear which the operator clicks on, or via which the operator indicates agreement with the simulated work step or the shown work step. If agreement by the operator is present, the work step is made final or automatically implemented.

Moreover, the operator can be assisted by an automatic comparison of acquired and/or to-be-processed data with reference data, in particular by an image data comparison. In this case the program (which for this purpose possibly includes databases or has access to such) implements a data comparison with data already present in databases or at other locations. For example, the data comparison serves to detect similarities or, respectively, correlations. Image data can in particular be compared which, for example, are based on the same image acquisition protocol or show the same or similar anatomical regions. The comparison result subsequently serves to assess the quality of the data acquisition or to identify subsequent work steps, for example.

The data comparison can be implemented for anatomical data and/or with reference data of an anatomical atlas. If anatomical data are acquired in the framework of an image data acquisition, these are particularly suited for a comparison that is implemented by the program since the variegated information that is available in images can hardly be detected by an operator with the reliability and as quickly as this is possible with the aid of a computer.

In the inventive method, anatomical data can be compared with reference data of an anatomical atlas. For example, the object can be posed to identify an atrium in a slice image of the heart that shows outgoing vessels. A help atlas or anatomical atlas can be used for this purpose by the program accessing automatically, or after a corresponding request by the operator. For this the operator can, for example, specify that the anatomical structure sought by the operator is the atrium. This can ensue by selection from a list that the program provides, or by input in a text field or the like. An automatic identification of the image data with the inventive method can thereupon ensue by an internal comparison with the anatomical atlas. The information so acquired can be provided to the operator as an aid.

According to the invention, in the framework of the comparison the data acquired and/or to be acquired can thus be automatically identified and/or resulting correlations between the acquired and/or to-be-acquired data and reference data can be rendered as a comparison result in a presentation on a monitor of the computer, in particular via at least one emphasis and/or marking of acquired data in a presentation. By the access to reference data it can thus automatically be established by the program that, for example, these are image data of a specific image acquisition method or a specific anatomical structure. Other measurement data can likewise be associated by comparison with comparison values, for example using an analysis of their values. The program can in turn derive a correct workflow therefrom.

If sufficient correlations are detected in the framework of the comparison that concern, for example, both the already acquired or still expected values of the data to be acquired, these correlations or information following from them can be presented or displayed on a monitor. Given image data this can ensue by presenting an anatomical structure identified via the comparison in an emphasized manner in an image. For example, a marking or a coloration or the like can occur. Given numerical values, correlations can likewise be shown emphasized via a particular color presentation or direct comparison.

Moreover, the operator can be assisted dependent on at least one recording (in particular a video recording) of work steps, in particular a recording of work steps of an experienced operator, that is accessible to the program. The possibility thus exists that an experienced user or operator of a medical device (for example an image acquisition device) can record his or her workflow as a video given the data acquisition or data post-processing by the system. This video can be provided by the program to assist the current operator.

In the event that the program has detected errors or, respectively, a delay of the implementation of the work steps by the operator, this video is automatically displayed to the operator upon request.

The assistance can also ensue via a presentation of at least one recording on a monitor for viewing by the operator.

Furthermore, the at least one recording of work steps to assist the operator can be evaluated by the program, in particular by a subdivision into individual work steps and/or sub-steps and/or a comparison with at least one already effected and/or to-be-effected work step of the operator. The program thus accesses the video or film recordings of the experienced operator and evaluates these, for example by a comparison with the actions of the current operator. A subdivision of the recordings into individual work steps or sub-steps can in particular be meaningful. This sub-division can be used to display only the respective relevant step form the recording to the current operator. Furthermore, a specific number of work steps that are to be executed subsequently or possibly differently can be displayed dependent on the subdivision. For a work step of the operator that is yet to be effected, a comparison can already be implemented during the course of the step or the comparison can be prepared in advance and/or can be implemented in a predictive manner.

If an inexperienced user now requires help at one point in the workflow, the next workflow step is presented to him or her such that the appertaining segment is displayed as a video sequence of precisely the desired work step. The inexperienced user thus sees how an experienced user has proceeded in the workflow. Work steps that are still to be effected (that the program has identified as such) can accordingly be displayed dependent on already-occurred work steps.

Furthermore, given a number of accessible recordings at least one recording and/or at least one part of a recording can be selected (in particular for presentation on a monitor) dependent on the evaluation. In this case the program thus has access to a number of film or video sequences from which it selects a suitable work step or suitable work steps and sub-steps. The program thus implements a comparison of the present recordings or their content with the work steps that the operator has already effected or that the operator must still implement or that are expected dependent on a superordinate operating method in which the operator is involved, for example an image post-processing protocol or the like.

In an embodiment the operator is assisted by at least one operating instruction accessible to the program with regard to at least one already-effected and/or still-to-be-effected work step by storage on a computer or external data access, in particular by a presentation of the operating instruction (which possibly exists as a video recording) on a monitor.

This enables department-internal, standardized operating instructions that every operator must carry with him or her or to which every operator must have access to be stored in electronic form directly at the medical device, such that the operating instructions are available at any time for every operator or employee of the department without him or her having to be elaborately sought out. In contrast to a text presentation (which is naturally likewise possible), a visualized presentation of these operating instructions (for example as a video) offers the advantage that this is didactically better ascertainable and simpler to understand. The desired result (for example the assurance of a high image quality given the acquisition of image data in order to achieve a reliable diagnosis) thus can be safely obtained.

The inventive method therefore offers the advantage that the implementation of a workflow or of a series of operating steps is significantly simplified for an operator. For example, if the operator arrives at a point in the workflow at which he or she is at a loss, the operator can resort to the interactive help or this can automatically help the operator further. Because the program tracks the actions of the user, it provides assistance precisely at the point in the workflow that is relevant for the user. The system of the computer wholly automatically takes over the next work step or shows a video of a subsequent step that was recognized by the program to be reasonable and, for example, was recorded in a workflow of an experienced operator, and/or the program identifies anatomical regions in images and the like. This makes it possible, even for workflows that are implemented rather rarely or require a particular training, to be implemented quickly and without great effort with the inventive method. The previously described documentation of standardized workflows can be stored in electronic form directly on the medical device and can be visualized as needed.

Moreover, the invention concerns a medical device, in particular a medical image data acquisition device, with a computer that is in particular fashioned to implement a method as described in the preceding, in which medical device at least one work steps already effected and/or still to-be-effected by an operator at the computer can be determined and/or analyzed in the framework of controlling the data acquisition and/or the data processing on the part of the program of the device, which is stored on the computer and/or to which the computer has access, and the operator is assisted dependent on the determination and/or analysis result.

For example, the inventive device can be an image data acquisition device such as a magnetic resonance tomography apparatus or a computed tomography apparatus or the like. The medical device has a computer which can be, for example, a control console for the data acquisition and possibly also for the subsequent processing. The computer can also be fashioned such that, in addition to a control console, one or more workstations for the data post-processing are provided. A program is stored on the computer or the computer has access via a data connection to a program that affords an interactive help for the work steps of the operator such that the actions of the operator are tracked in the background (possibly after a request by the operator) or given an active request it is checked where this operator is situated in the workflow. It is likewise or additionally possible that a comparison with reference data is implemented by the computer, which is correspondingly fashioned for this purpose and in particular possesses databases that contain such data or, respectively, has access to such. A subsequent work step or, respectively, a comparison result is presented via a monitor of the medical device. Regions detected in the framework of a comparison can likewise be shown marked.

Furthermore, in the inventive device it is possible that videos can be displayed of standardized operating instructions or of work steps of an experienced operator that are stored on the computer or to which the computer has access.

With the inventive medical device it is thus possible to control the data acquisition or data processing in a manner that is precise and adapted to the individual operator, so a qualitatively high-grade data acquisition and further data processing can be ensured.

BRIEF DESCRIPTION OF THE DRAWINGS

FIG. 3 shows a further embodiment of the workflow of an inventive method for controlling the data acquisition or data processing in a C-arm system.

DESCRIPTION OF THE PREFERRED EMBODIMENTS

Figure 1:
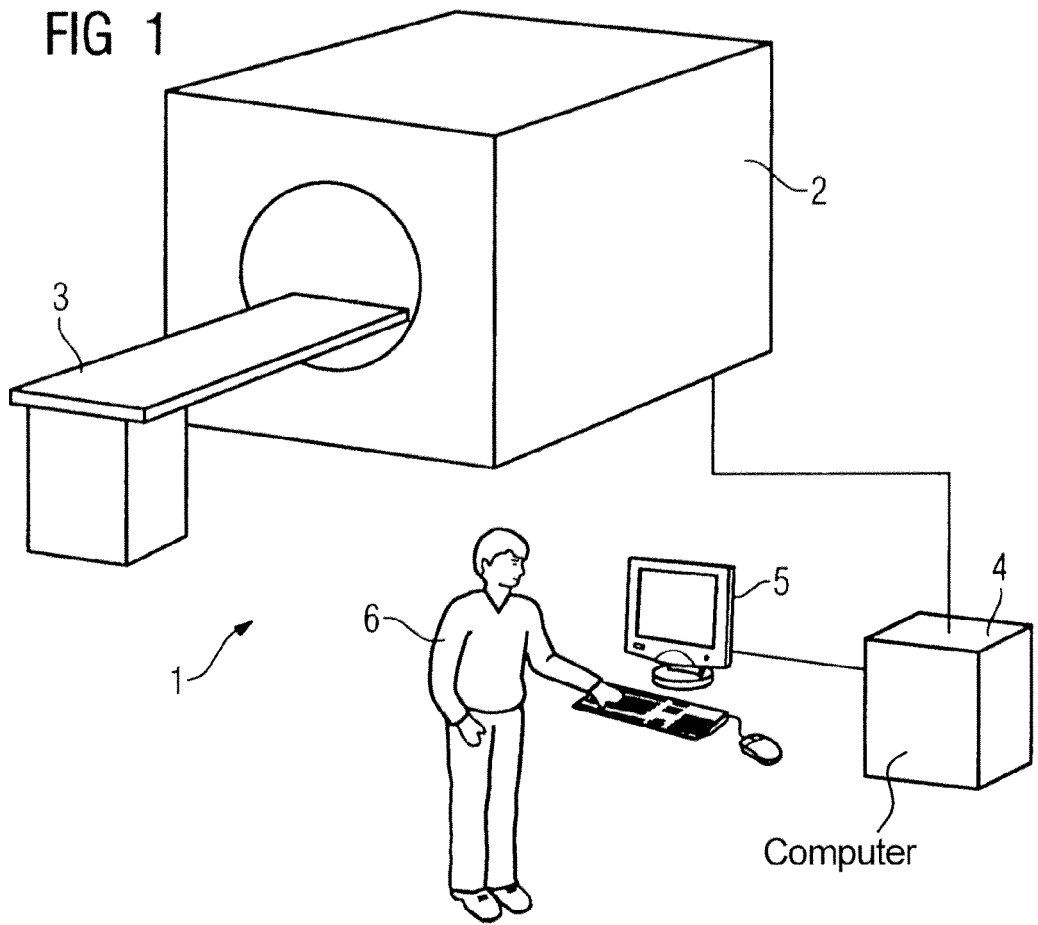
FIG. 1 shows a medical device according to the invention.

An inventive medical device 1 is shown in FIG. 1. The medical facility 1 has an image data acquisition apparatus 2 which here is a magnetic resonance tomography apparatus in which a patient (not shown) is borne on the patient bed 3 for the image data acquisition. The medical device 1 furthermore has a computer 4 that communicates with the image data acquisition apparatus 2 via a data connection. A monitor 5 for the operation by an operator 6 is connected in turn to the computer 4. For this the monitor 5 also comprises an operator controls for the operator 6.

If an image data acquisition should now be effected with the image data acquisition apparatus 2, this requires the implementation of work steps on the part of the operator 6. For example, inputs with regard to the identity or the present illness of a patient are to be made or retrieved. Furthermore, a series of examination protocols is to be selected. The image acquisition parameters must possibly be adapted specific to the patient or dependent on a region to be acquired. Overall a more complex workflow is required that is inventively simplified in that a program with which the operator 6 is provided with interactive help is stored on the computer 4.

For this purpose, the program on the computer 4 tracks the actions of the operator 6. As in the present case this possibly does not occur automatically at all times but rather dependent on a request on the part of the operator 6 who communicates this to the program via the operator controls of the monitor 5.

The operator 6 thereby receives precisely the help that he or she requires, for example via a simulation of a further work step that is recognized as reasonably to follow by the program on the computer 4. The simulated work step can possibly be directly adopted. For this the operator 6 declares his agreement by clicking on an agreement field (not shown here) on the monitor 5.

In the shown case the subsequent post-processing of the image data acquired with the image data acquisition apparatus 2 is likewise implemented via the computer 4 with the monitor 5.

In other medical devices this can also be effected at workstations or separate computers provided separately for the image post-processing.

This post-processing of the image data is also assisted by the program on the computer 4. The work steps that the operator 6 implements are determined or, respectively, analyzed. The program can thus detect that the operator 6 is located in a segmentation phase in the post processing or the like. If the operator 6 requires help, an automatic identification of a sought anatomical structure is offered to him on the part of the computer 4 in the segmentation via an image data comparison with reference data present in a database. Further work steps are displayed as a video on the part of the program on the computer 4 as the operator 6 desires.

Rare or elaborate workflows thus can also be implemented while assuring a high quality standard for the data acquisition or processing.

Figure 2:
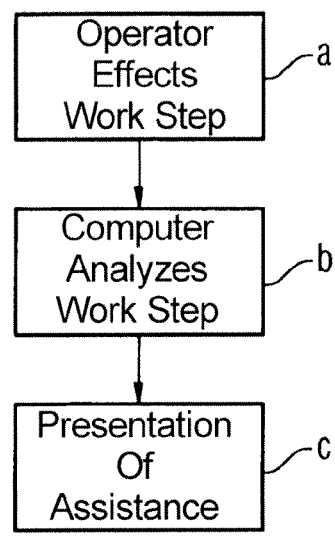
FIG. 2 shows the basic steps of the workflow of a method according to the invention.

FIG. 2 shows a principle drawing of the workflow of an inventive method. According to step a the operator thereby effects a work step at a computer of a medical device that is operated via a keyboard and control implements. According to step b this work step is determined and analyzed on the part of a program that is stored on the computer or to which access is available to the computer in other embodiments of the method. The computer thus establishes which work step was effected and evaluates this.

If, in an inventive method according to the step a, a number of work steps are executed or a work step is executed that can be definitively associated with a specific workflow, in step b the program determines further work steps that are still to be effected in the event that this is desired by an operator.

According to step c, the program derives a result from the determination or analysis, thus detects whether this step is reasonable or was implemented in an unconventional manner in comparison to the preceding steps, and the program offers corresponding assistance to the operator. This assistance appears such that the control implement of the user is (automatically) directed, a video is displayed or a reference data comparison is initiated depending on the result. This enables the operator to be interactively assisted in an uncomplicated manner in workflows in which he feels unsure.

FIG. 3 shows a further drawing of the workflow of an inventive method to control the data acquisition or, respectively, data processing in a C-arm system 7. The C-arm system 7 possesses a patient bed 8 as well as a computer 9 that is coupled with the C-arm 10 of the C-arm system 7 via a data connection.

Connected to the computer 9 is a monitor 11 with whose help the work steps to control the data acquisition and data processing with the C-arm system 7 are implemented via the control implements 12a and 12b on the part of the operator 13.

In the present case images 14a and 14b acquired with the aid of the C-arm 10 are presented on the monitor 11 for this. The operator 13 who has presently already implemented the data acquisition must now subject these already-acquired images 14a and 14b to a further processing.

When the operator 13 runs into problems in the work steps, a program on the computer 9 that has tracked the actions of the operator 13 automatically engages. In the present case it simulates a subsequent workflow step that (as indicated by the arrow 15) leads to processed images 16a and 16b on the monitor 11. For this the program on the computer 9 takes over the direction of the control implement 12b, as is indicated here by the mouse arrow 17.

By clicking on a box 18 in the subsequent step according to the arrow 19, the operator 13 declares his agreement with the automatically effected action. This is then ultimately adopted. The images are stored on the computer in the processed form as processed images 16a and 16b.

Alternatively or additionally, according to the arrows 20 and 21 the program can offer the operator 13 assistance in a different manner.

According to the arrow 20, a box 22 in which anatomical structures are listed is displayed to the operator 13 on the monitor 11 for the acquired images 14a and 14b. The operator 13 subsequently selects such an anatomical structure, whereupon the program of the computer 9 accesses an anatomical atlas with whose help the desired anatomical structure is identified in the acquired images 14a or 14b. This is subsequently shown marked in the images 14a and 14b as the operator 13 desires.

According to the arrow 21, a video 23 that shows the work step that the operator has to effect in the following as a recording of an experienced operator is shown to the operator on the monitor 11 for the processing of the acquired images 14a and 14b. By following this video 23 the operator 13 (who is inexperienced in the implementation of this work step) can correctly implement the required work step at his end by reproducing the actions of the experienced operator.

In particular workflows that occur rarely or that require a particular training thus can be implemented very quickly and without greater effort given optimal results.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a medical image data acquisition device, comprising the steps of:

through entries made by an operator via a computer, controlling a data handling procedure, selected from the group consisting of data acquisition and data processing, executed by a medical image data acquisition device, said data handling procedure comprising a plurality of work steps executed in sequence;

for an entry made by the operator, among said entries, that designates at least one of said work steps selected from the group consisting of an entry for a work step already effected by the operator and an entry for a work step yet to be effected by the operator, automatically determining in said computer that the operator requires assistance in implementing said at least one of said work steps, by executing a program in said computer that analyzes said entry in context with at least one of steps previously performed by the operator via the computer and a data acquisition protocol entered into the computer for said data acquisition to detect when said entry is atypical or erroneous and thereupon automatically generating an analysis result dynamically selected, dependent on said context, from the group consisting of determination of at least one work step that should be implemented from among said plurality of work steps, and analysis information; and from said computer, making said analysis result available to the operator in a humanly perceptible form.

2. A method as claimed in claim 1 comprising initiating execution of said analysis within said program in response to an input by the operator into the computer selected from the group consisting of confirmation of a need for assistance in response to a prompt presented by the program via the computer to the operator, and an assistance request.

3. A method as claimed in claim 1 comprising, if said analysis result is determination of at least one work step that should be implemented from among said plurality of work steps, automatically executing, via said program, said work step that should be implemented, and, if said analysis result is said analysis information, making said analysis information visually perceptible to the operator as a simulation of at least one work step from among said plurality of work steps.

4. A method as claimed in claim 1 comprising, if said analysis result is said determination of at least one work step that should be implemented from among said plurality of work steps, including, in said presentation of said analysis result, a prompt requiring confirmation by the operator to implement said work step that should be implemented, and implementing said work step that should be implemented upon entry of said combination by the operator in response to said prompt.

5. A method as claimed in claim 1 comprising implementing said analysis in said computer with said program by automatically comparing data to be handled by said data handling procedure with reference data.

6. A method as claimed in claim 5 wherein said data to be handled by said data handling procedure comprise anatomical data, and comprising comparing said anatomical data with data from an anatomical atlas, as said reference data.

7. A method as claimed in claim 5 wherein comparison of said data to be handled by said handling procedure with said reference data produces a comparison result, and comprising presenting said comparison result as part of said presentation of said analysis result.

8. A method as claimed in claim 7 comprising presenting said analysis result with said comparison result as a visual display at a monitor connected to the computer, and presenting said comparison result as at least one of an emphasis and a marking in a presentation of said data to be handled by said handling procedure.

9. A method as claimed in claim 1 comprising causing, via said program in said computer, said presentation of said analysis result as a video recording of at least some of plurality of work steps, said video recording being accessible in said computer from said program.

10. A method as claimed in claim 9 comprising presenting said video recording at a monitor connected to said computer.

11. A method as claimed in claim 9 comprising, during execution of said program in said computer, comparing steps in said video recording to said work step for which said operator requires assistance to obtain a comparison result, and presenting said video recording in said analysis result dependent on said comparison result.

12. A method as claimed in claim 11 comprising storing a plurality of video recordings in a memory accessible by execution of said program in said computer, and, depending on said analysis result, selecting one of said recordings.

13. A method as claimed in claim 1 comprising presenting said analysis result as an operating instruction in a format selected from the group consisting of text and video images.

14. A medical facility comprising:

a medical image data acquisition device;

an input unit and a computer connected thereto configured, through entries made by an operator via the computer, to control a data handling procedure, selected from the group consisting of data acquisition and data processing, executed by said medical image data acquisition device, said data handling procedure comprising a plurality of work steps executed in sequence;

said computer being configured, for an entry among said entries at least one of said work steps selected from the group consisting of an entry for a work step already effected by the operator and an entry for a work step yet to be effected by the operator, to automatically determine that the operator requires assistance in implementing said at least one of said work steps, by executing a program in said computer that analyzes said entry in context with at least one of steps previously performed by the operator via the computer and a data acquisition protocol entered into the computer for said data acquisition to detect whether said entry is atypical or erroneous and thereupon to generate an analysis result dynamically selected, dependent on said context, from the group consisting of determination of said at least one of said work steps and analysis information; and a display connected to said computer, at which said computer makes said analysis result available to the operator in a humanly perceptible form.

* * * * *